US 12,086,716 B1

(12) United States Patent
Liu et al.

(10) Patent No.: US 12,086,716 B1
(45) Date of Patent: Sep. 10, 2024

(54) METHOD FOR CONSTRUCTING MULTIMODALITY-BASED MEDICAL LARGE MODEL, AND RELATED DEVICE THEREOF

(71) Applicant: AthenaEyes CO., LTD., Changsha (CN)

(72) Inventors: Weihua Liu, Changsha (CN); Jianhua Qiu, Changsha (CN); Jinmin Ma, Changsha (CN)

(73) Assignee: AthenaEyes CO., LTD., Changsha (CN)

( * ) Notice: Subject to any disclaimer, the term of this patent is extended or adjusted under 35 U.S.C. 154(b) by 0 days.

(21) Appl. No.: 18/388,859

(22) Filed: Nov. 13, 2023

(30) Foreign Application Priority Data

May 25, 2023 (CN) .......................... 202310596917.1

(51) Int. Cl.
*G06N 3/08* (2023.01)
*G16H 50/70* (2018.01)

(52) U.S. Cl.
CPC .............. *G06N 3/08* (2013.01); *G16H 50/70* (2018.01)

(58) Field of Classification Search
CPC ................................ G06N 3/08; G16H 50/70
See application file for complete search history.

(56) References Cited

U.S. PATENT DOCUMENTS

2018/0322254 A1 11/2018 Smurro
2020/0335187 A1* 10/2020 Lefkofsky .............. G16H 50/50
2022/0012076 A1 1/2022 Natarajan et al.
2022/0114463 A1 4/2022 Tumuluri
2023/0042272 A1 2/2023 Mahadeva Cadwell
2024/0037336 A1* 2/2024 Akbari ................... G06N 3/045

FOREIGN PATENT DOCUMENTS

| CN | 107845422 A | 3/2018 |
| CN | 113851219 A | 12/2021 |
| CN | 114694076 A | 7/2022 |
| CN | 114898861 A | 8/2022 |
| CN | 115129839 A | 9/2022 |
| CN | 115438149 A | 12/2022 |

(Continued)

OTHER PUBLICATIONS

Helena Balabin et al. (book NPL "Multimodal Transformers for Biomedical Text and Knowledge Graph Data", Technical Report Feb. 2022 Hochschule Bonn-Rhein-Sieg University of Applied Sciences, Department of Computer Science) (Year: 2022).*

(Continued)

*Primary Examiner* — Michael J Huntley
*Assistant Examiner* — Imad Kassim
(74) *Attorney, Agent, or Firm* — Bayramoglu Law Offices LLC

(57) ABSTRACT

A method for constructing a multimodality-based medical large model, and a related device thereof are provided. The medical large model includes a multimodal transformer T, a prompt manager M, a dialogue engine L, a task controller H, and a multimodal foundation (MMF) that includes at least one medical foundation model (MFM). Five stages, namely modal analysis, model allocation, downstream task result feedback, modal transformation normalization, and response generation are designed.

20 Claims, 5 Drawing Sheets

(56) References Cited

FOREIGN PATENT DOCUMENTS

CN 116259407 A 6/2023
KR 20200049254 A 5/2020

OTHER PUBLICATIONS

Agrawal et al. (NPL "Large Language Models are Few-Shot Clinical Information Extractors", arXiv:2205.12689, Nov. 30, 2022) (Year: 2022).*
Ali et al. ("Multi-model-based interactive authoring environment for creating shareable medical knowledge", vol. 150, Oct. 2017, pp. 41-72) (Year: 2017).*

* cited by examiner

METHOD FOR CONSTRUCTING MULTIMODALITY-BASED MEDICAL LARGE MODEL, AND RELATED DEVICE THEREOF

CROSS REFERENCE TO THE RELATED APPLICATIONS

This application is based upon and claims priority to Chinese Patent Application No. 202310596917.1, filed on May 25, 2023, the entire contents of which are incorporated herein by reference.

TECHNICAL FIELD

The present disclosure relates to the field of data processing, and in particular to a method for constructing a multimodality-based medical large model, and a related device thereof.

BACKGROUND

With the development of artificial intelligence (AI), deep learning (DL) has made significant progress in various AI research fields, such as computer vision (CV) and natural language processing (NLP). For example, deep residual networks (ResNets) have surpassed human performance in image classification. The emergence of large language models (such as chat generative pre-trained transformer (chatGPT) and generative pre-trained transformer 4 (GPT-4)) has driven the rapid development of NLP. Based on a large corpus of online text data and powerful architecture, large language models can read, write, and converse like humans. Among them, robustly optimized bidirectional encoder representations from transformers (BERT) pre-training approach (RoBERTa4), performs better than humans in several natural language understanding (NLU) tasks of general language understanding evaluation (GLUE). The relational network is designed by DeepMind, and achieves performance beyond humans on relational reasoning datasets. Since the data information of various modalities may be produced in the process of medical diagnosis and treatment, the medical large model needs a multimodality processing. The multimodality-based medical large model combines text, audio, image, video and other multimodality data for learning, combines a variety of perceptual approaches and forms of expression, so that the information from different perception channels (such as vision, hearing, language and touch, etc.) can be processed and understood at the same time, and expressed and output in a multimodality manner.

However, there are at least the following technical issues in the prior art. That is, in practical application scenarios, the data modality is not limited to text. Although audio, image, and video are equally important, most existing advances in AI only focus on a single cognitive ability. The current technological development of AI often only focuses on the improvement of a single cognitive ability (such as image classification, language understanding, or audio processing) to approach or surpass human intelligence (HI). Taking ChatGPT as an example, since it is trained using language, it is currently unable to process or generate images and audio in the seeing and hearing worlds. Meanwhile, although visual basic models, such as visual transformer or stable diffusion, exhibit strong visual understanding and generation capabilities, they only have the ability to perform specific tasks with fixed inputs and outputs in one round and cannot perform multiple rounds of task processing.

SUMMARY

Embodiments of the present disclosure provide a method and apparatus for constructing a multimodality-based medical large model, a computer device, and a storage medium to achieve multimodal task processing and improve processing efficiency.

In order to solve the above technical problem, an embodiment of the present disclosure provides a method for constructing a multimodality-based medical large model, where the multimodality-based medical large model includes a multimodal transformer T, a prompt manager M, a dialogue engine L, a task controller H, and a multimodal foundation (MMF); the MMF includes at least one medical foundation model (MFM); the MFM includes basic models for a downstream task, and a medical language module (MLM); and the method for constructing a multimodality-based medical large model includes:

in a first stage, modal analysis: performing, by the multimodal transformer T, modal analysis on input query information to determine a task type;

in a second stage, model allocation: selecting, by the task controller H and the prompt manager M, a model Pp and a corresponding parameter hPp for task processing, and allocating a resource corresponding to the task type to the model Pp, where the model Pp is one of the basic models for the downstream task;

in a third stage, downstream task result feedback; executing, by the MFM, the model Pp to generate a task output result oPp, and feeding back the task output result oPp to the MMF;

in a fourth stage, modal transformation normalization: extracting, by the MLM, an entity-related text span from the task output result oPp sent by the MMF to acquire a structured entity; annotating the structured entity to generate a feedback text; and feeding back the feedback text to the MMF; and in a fifth stage, response generation: receiving, by the MLM, a query result transmitted by the MMF, generating a professional response corresponding to the query result based on a medical knowledge base, and feeding back the professional response to a user.

Optionally, the performing, by the multimodal transformer T, modal analysis on input query information to determine a task type includes:

transforming, by the multimodal transformer T, the input query information into a query description $q_n^{(d)}$) and a set of query-related resources $(q_n^{(s1)}, q_n^{(s2)}, \ldots, q_n^{(sk)})$ of size k, where the query description $q_n^{(d)}$) is in vectorized form, and the input query information is in form of at least one of text, audio, and image; and performing a modal check on the query description $q_n^{(d)}$) to determine the task type.

Optionally, the multimodal transformer T is provided with a discriminator, and the performing a modal check on the query description $q_n^{(d)}$) to determine the task type includes:

semantically aligning the query description $q_n^{(d)}$) to acquire a new query; and discriminating, by the discriminator, the new query to determine the task type.

Optionally, the selecting, by the task controller H and the prompt manager M, a model Pp and a corresponding parameter hPp for task processing includes:

determining, by the task controller H, a type of each of the query-related resources $\{q_n^{(s1)}, q_n^{(s2)}, \ldots, q_n^{(sk)}\}$ to determine different task families; and transferring, for a selected task family, the query description $q_n^{(d)}$) corresponding to the task family to the prompt manager M to generate a parameter, including the selected model Pp and corresponding parameter hPp, where p denotes a task model set $\{p_i\}_{i=1}^{P}$ to which the selected model belongs; hPp denotes the task family selected by a task handler H; P denotes a number of models; and i is a positive integer within [1,P].

Optionally, the basic models for the downstream task include a visual task model and an audio task model; the visual task model is configured to detect and segment a biomarker in a medical image, and is further configured to analyze and acquire blood pressure, heart rate, and health indicator parameters based on a facial video; and the audio task model is configured to identify audio.

Optionally, the generating a professional response corresponding to the query result based on a medical knowledge base, and feeding back the professional response to a user includes:

outputting, in terms of an audio task, a waveform of a displayed image and an identification result of corresponding audio, and generating corresponding text information as the professional response corresponding to the query result for feedback;

feeding back, in terms of a text task, a transcribed text as the professional response corresponding to the query result for feedback;

displaying, in terms of a visual task, an output video and a related image frame; invoking a corresponding visual task model of the MFM, and feeding back a result to the MMF; and generating, by the MMF, a text dialogue based on modal transformation of the result, as the professional response corresponding to the query result for feedback; and displaying, in terms of a medical image tumor detection task, a segmented posterior image within a time span, and generating, by the MLM, a corresponding text content based on an image segmentation result, as the professional response corresponding to the query result for feedback.

In order to solve the above technical problem, an embodiment of the present disclosure further provides an apparatus for constructing a multimodality-based medical large model, where the multimodality-based medical large model includes a multimodal transformer T, a prompt manager M, a dialogue engine L, a task controller H, and an MMF; the MMF includes at least one MFM; the MFM includes basic models for a downstream task, and an MLM; and the apparatus for constructing a multimodality-based medical large model further includes:

a modal analysis module, configured to perform, by the multimodal transformer T, modal analysis on input query information to determine a task type;

a model allocation module, configured to select, by the task controller H and the prompt manager M, a model Pp and a corresponding parameter hPp for task processing, and allocate a resource corresponding to the task type to the model Pp, where the model Pp is one of the basic models for the downstream task;

a downstream task result feedback module, configured to, execute, by the MFM, the model Pp to generate a task output result oPp, and feed back the task output result oPp to the MMF;

a modal transformation normalization module, configured to extract, by the MLM, an entity-related text span from the task output result oPp sent by the MMF to acquire a structured entity, annotate the structured entity to generate a feedback text; and feed back the feedback text to the MMF; and a response generation module, configured to receive, by the MLM, a query result transmitted by the MMF, generate a professional response corresponding to the query result based on a medical knowledge base, and feed back the professional response to a user.

Optionally, the modal analysis module includes:

an information transformation sub-module, configured to transform, by the multimodal transformer T, the input query information into a query description $q_n^{(d)}$) and a set of query-related resources $\{q_n^{(s1)}, q_n^{(s2)}, \ldots, q_n^{(sk)}\}$ of size k, where the query description $q_n^{(d)}$ is in vectorized form, and the input query information is in form of at least one of text, audio, and image; and a modal check sub-module, configured to perform a modal check on the query description $q_n^{(d)}$ to determine the task type.

Optionally, the multimodal transformer T is provided with a discriminator, and the modal check sub-module includes:

a semantical aligning unit, configured to semantically align the query description $q_n^{(d)}$ to acquire a new query; and a discrimination unit, configured to discriminate, by the discriminator, the new query to determine the task type.

Optionally, the model allocation module includes:

a task family determination unit, configured to determine, by the task controller H, a type of each of the query-related resources $\{q_n^{(s1)}, q_n^{(s2)}, \ldots, q_n^{(sk)}\}$ to determine different task families; and a model selection unit, configured to transfer, for a selected task family, the query description $q_n^{(d)}$ corresponding to the task family to the prompt manager M to generate a parameter, including the selected model Pp and corresponding parameter hPp, where p denotes a task model set $\{p_i\}_{i=1}^{P}$ to which the selected model belongs; hPp denotes the task family selected by a task handler H; P denotes a number of models; and i is a positive integer within [1,P].

Preferably, the response generation module includes:

a first generation unit, configured to output, in terms of an audio task, a waveform of a displayed image and an identification result of corresponding audio, and generate corresponding text information as the professional response corresponding to the query result for feedback;

a second generation unit, configured to feed back, in terms of a text task, a transcribed text as the professional response corresponding to the query result for feedback;

a third generation unit, configured to display, in terms of a visual task, an output video and a related image frame; invoke a corresponding visual task model of the MFM, and feed back a result to the MMF; and generate, by the MMF, a text dialogue based on modal transformation of the result, as the professional response corresponding to the query result for feedback; and a fourth generation unit, configured to display, in terms of a medical image tumor detection task, a segmented posterior image within a time span, and generate, by the MLM, a corresponding text content based on an image segmentation result, as the professional response corresponding to the query result for feedback.

In order to solve the above technical problem, an embodiment of the present disclosure further provides a computer device. The computer device includes a memory, a processor, and a computer program stored in the memory and executable on the processor, where the processor executes the computer program to perform the steps of the method for constructing a multimodality-based medical large model.

In order to solve the above technical problem, an embodiment of the present disclosure further provides a computer-readable storage medium. The computer-readable storage medium stores a computer program, where the computer program is executed by a processor to implement the steps of the method for constructing a multimodality-based medical large model.

The embodiments of the present disclosure provide a method and apparatus for constructing a multimodality-based medical large model, a computer device, and a storage medium. The medical large model includes a multimodal transformer T, a prompt manager M, a dialogue engine L, a task controller H, and an MMF. The MMF includes at least one MFM. The present disclosure designs five stages, namely modal analysis, model allocation, downstream task result feedback, modal transformation normalization, and response generation. The present disclosure processes multimodal data simultaneously and fully utilizes the correlation between the multimodal data to achieve rapid multimodal task processing, improving the intelligent processing level and processing efficiency for artificial intelligence (AI) tasks.

BRIEF DESCRIPTION OF THE DRAWINGS

To describe the technical solutions in the embodiments of the present disclosure more clearly, the following briefly describes the drawings required for describing the embodiments or the prior art. Apparently, the drawings in the following description show merely some of the embodiments of the present disclosure, and those of ordinary skill in the art may still derive other drawings from these drawings without creative efforts.

DETAILED DESCRIPTION OF THE EMBODIMENTS

Unless otherwise defined, all technical and scientific terms used in the present disclosure have the same meanings as commonly understood by those skilled in the technical field of the present disclosure. The terms used in the specification of the present disclosure are merely intended to describe the specific embodiments, rather than limit the present disclosure. The terms "includes" and "has" in the specification, claims, and drawings of the present disclosure and any variations thereof are intended to encompass without excluding other content. Terms such as "first" and "second" in the specification and claims or the drawings of the present disclosure are intended to distinguish different objects, rather than to describe a specific order.

The term "embodiment" mentioned herein means that a specific feature, structure, or characteristic described in combination with the embodiment may be included in at least one embodiment of the present disclosure. The phrase appearing in different parts of the specification does not necessarily refer to the same embodiment or an independent or alternative embodiment exclusive of other embodiments. It may be explicitly or implicitly appreciated by those skilled in the art that the embodiments described herein may be combined with another embodiment.

The technical solutions in the embodiments of the present disclosure are described clearly and completely below with reference to the drawings in the embodiments of the present disclosure. Apparently, the described embodiments are merely a part rather than all of the embodiments of the present disclosure. All other embodiments obtained by those of ordinary skill in the art based on the embodiments of the present disclosure without creative efforts should fall within the protection scope of the present disclosure.

Figure 1:
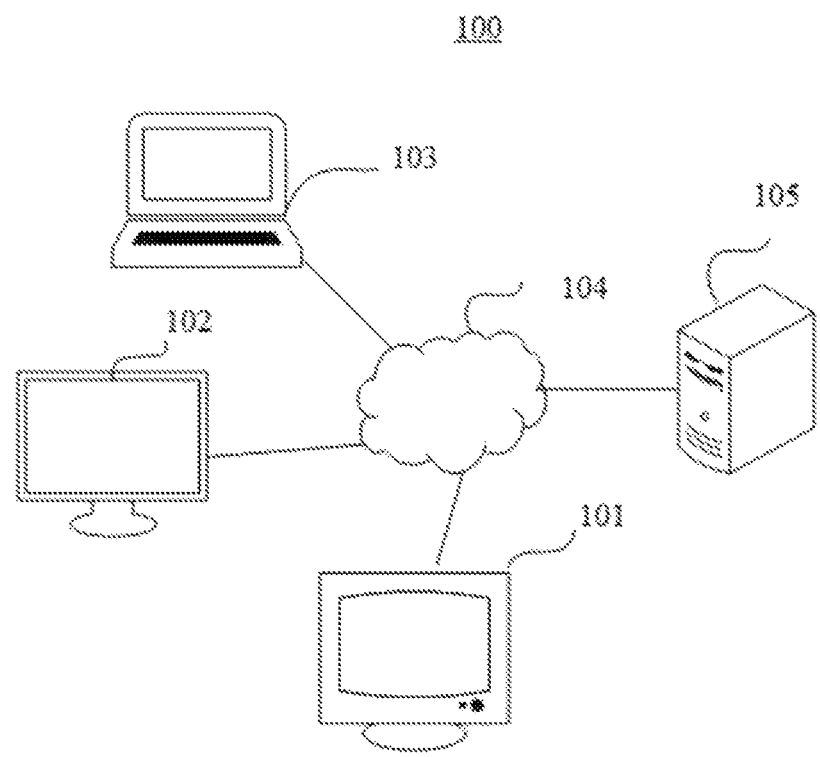
FIG. 1 is a diagram of an exemplary system architecture to which the present disclosure can be applied.

Referring to FIG. 1, FIG. 1 shows system architecture 100, which may include terminal devices 101, 102, and 103, network 104, and server 105. The network 104 is configured to provide a medium of a communication link between the server 105 and the terminal devices 101, 102, and 103. The network 104 may have various connection types, for example, a wired or wireless communication link or a fiber-optic cable, etc.

A user can interact with the server 105 through the network 104 via the terminal devices 101, 102, and 103 to receive or send a message, etc.

The terminal devices 101, 102, and 103 can be various electronic devices that are provided with a display screen and support web browsing, including but not limited to smartphones, tablet computers, e-book readers, moving picture experts group audio layer III (MP3) players, moving picture experts group audio layer IV (MP4) players, laptop computers, and desktop computers.

The server 105 can be a server that provides various services, such as a backend server that supports pages displayed on the terminal devices 101, 102, and 103.

It should be noted that the method for constructing a multimodality-based medical large model according to the embodiment of the present disclosure is implemented by the server, and correspondingly, the apparatus for constructing a multimodality-based medical large model is provided in the server.

It should be appreciated that the quantities of the terminal devices, the networks, and the servers in FIG. 1 are merely an example. Any quantities of terminal devices, networks, and servers may be provided according to implementation requirements. In the embodiment of the present disclosure, the terminal devices 101, 102, and 103 can specifically correspond to application systems in actual production.

Figure 2:
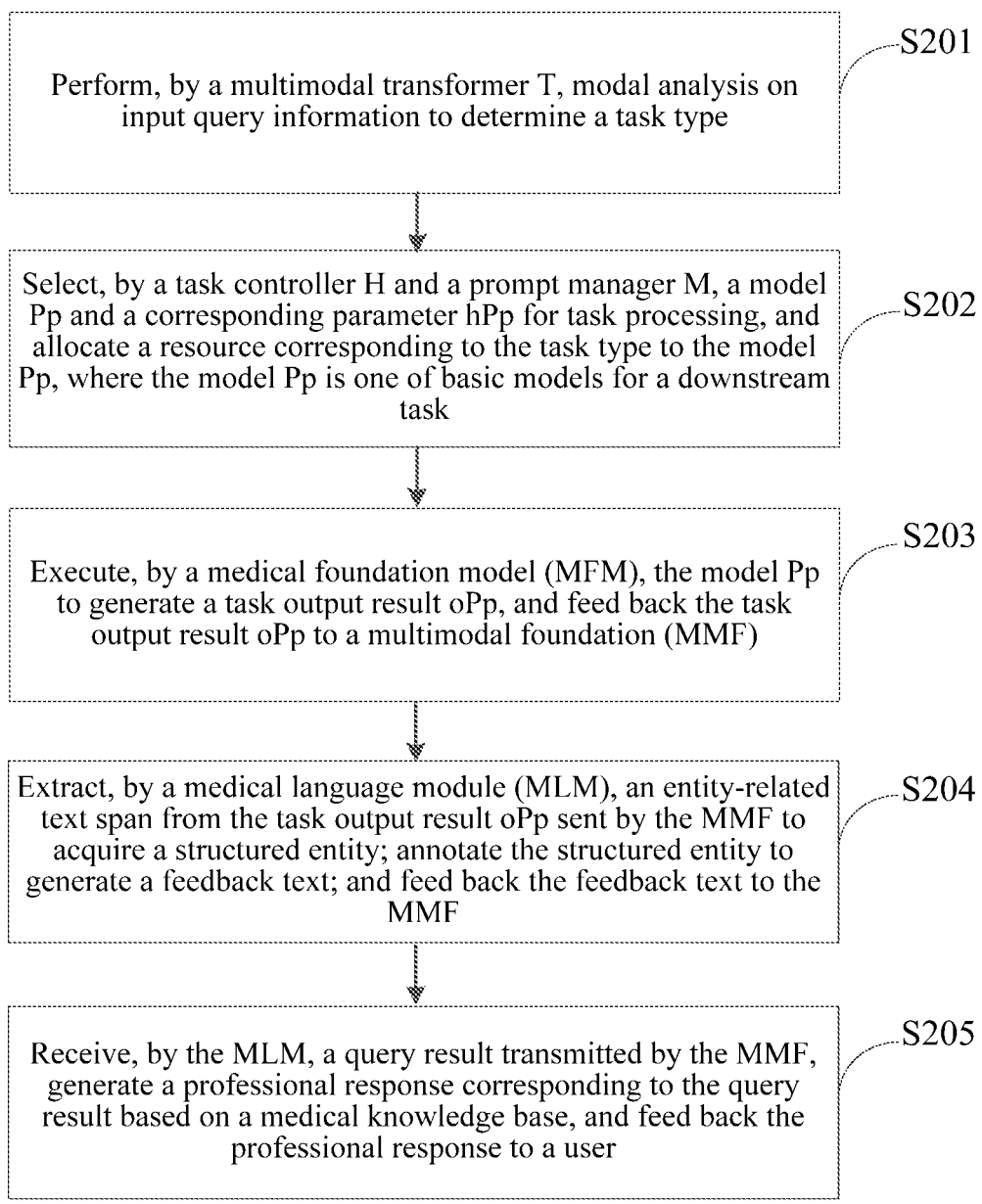
FIG. 2 is a flowchart of an embodiment of a method for constructing a multimodality-based medical large model according to the present disclosure.
Figure 3:
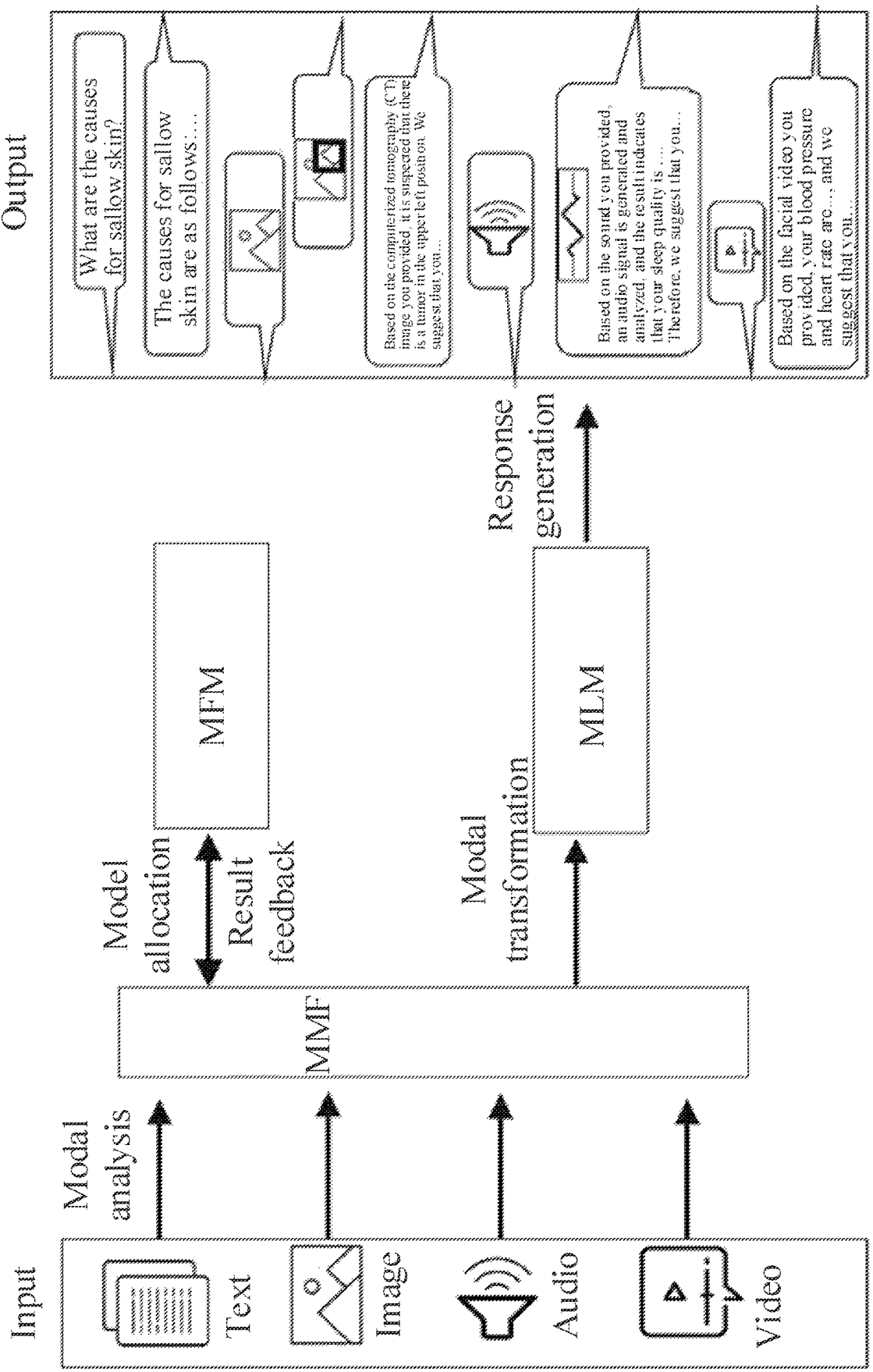
FIG. 3 is a schematic diagram of an application example of the method for constructing a multimodality-based medical large model according to the present disclosure.

Referring to FIGS. 2 and 3, FIG. 2 is a flowchart of a method for constructing a multimodality-based medical large model according to an embodiment of the present disclosure, and FIG. 3 is a schematic diagram of an application example of the method for constructing a multimodality-based medical large model according to the present disclosure. Taking the application of the method in a server side shown in FIG. 1, the multimodality-based medical large model includes a multimodal transformer T, a prompt manager M, a dialogue engine L, a task controller H, and a multimodal foundation (MMF). The MMF includes at least one medical foundation model (MFM). The MFM includes basic models for a downstream task, and a medical language module (MLM).

The MMF is responsible for performing modal analysis and task analysis on the query input (modal analysis stage), and invoking corresponding task model XS of the basic modules (model allocation stage). The MMF is provided with a visual basic model for images (such as medical images like computerized tomography (CT) images, magnetic resonance imaging (MRI) images, and facial videos, etc.) to process a complex downstream visual task, such as detecting and segmenting a biomarker (tumor) in the medical image or acquiring blood pressure, heart rate, etc. based on facial video analysis. The MMF is provided with an audio basic model for processing a complex audio task, such as monitoring sleep status based on a respiratory sound. A processing result of the basic model is fed back to the MMF (result feedback stage). The MFM performs modal transformation based on the processing result of the visual or audio task (modal transformation stage), and generates a language dialogue to interact with the user based on a medical knowledge base and the task processing result (response generation stage).

In a specific example, each input is expressed as dialogue query qi, where i denotes an i-th round of query, and each output is expressed as dialogue response ri. A contextual dialogue with (n−1) rounds of interactions is defined as C={(q1,r1), (q2,r2), . . . , (qn−1,rn−1)}. The query is resolved into structured parameter an of the task controller H by the dialogue engine L and the prompt manager M. The task controller H sends the structured parameter an to a corresponding audio task handler. After an execution procedure, the dialogue engine L performs modal transformation based on information from (q(n),C,Ps(an)). Finally, the MLM generates final response rn based on the knowledge base.

In this embodiment, the method for constructing a multimodality-based medical large model specifically includes the following steps.

S201. In a first stage, modal analysis is performed. That is, modal analysis is performed by the multimodal transformer T on input query information to determine a task type.

Specifically, in the first stage, the modal analysis is performed to accurately identify the input query information so as to determine the task type. The input query information is multimodal and may be any one or a combination of image, voice, video, and text. When an artificial intelligence (AI) task is processed, a prerequisite for accurate task generation and processing is to determine the modality included in the input query information.

The multimodal transformer can be implemented through various methods, such as vision transformer-based modal transformation and generative adversarial network (GAN)-based multimodal transformation, which are not limited herein.

In a specific optional implementation, in step S201, the modal analysis is performed on the input query information by the multimodal transformer T to determine a task type. This step includes:

The multimodal transformer T transforms the input query information into query description $q_n^{(d)}$ and a set of query-related resources $\{q_n^{(s_1)}, q_n^{(s_2)}, \ldots, q_n^{(s_k)}\}$ of size k, where the query description $q_n^{(d)}$ is in vectorized form, and the input query information is in form of at least one of text, audio, and image.

A modal check is performed on the query description $q_n^{(d)}$ to determine the task type.

In a specific optional implementation, the multimodal transformer T is provided with a discriminator, and the modal check is performed on the query description $q_n^{(d)}$) to determine the task type as follows.

The query description $q_n^{(d)}$ is semantically aligned to acquire a new query.

The new query is discriminated by the discriminator to determine the task type.

Semantical alignment refers to a procedure of preprocessing the query description $q_n^{(d)}$ to facilitate the subsequent discriminative comparison. Specifically, transformation processing is performed by an alignment module. The alignment module can be set according to actual needs, such as through a transformer network or an encoder.

In this embodiment, after semantical alignment, the discriminator discriminates the query to improve the accuracy of task type determination.

S202. In a second stage, model allocation is performed. That is, the task controller H and the prompt manager M select model Pp and corresponding parameter hPp for task processing, and allocate a resource corresponding to the task type to the model Pp, where the model Pp is one of the basic models for the downstream task.

In a specific optional implementation, in step S202, the task controller H and the prompt manager M select the model Pp and the corresponding parameter hPp for task processing as follows.

The task controller H determines a type of each of the query-related resources $\{q_n^{(s_1)}, q_n^{(s_2)}, \ldots, q_n^{(s_k)}\}$ to determine different task families.

For a selected task family, the query description $q_n^{(d)}$) corresponding to the task family is transferred to the prompt manager M so as to generate a parameter, including the selected model Pp and corresponding parameter hPp, where p denotes a task model set $\{p_i\}_{i=1}^{P}$ to which to which the selected model belongs; hPp denotes the task family selected by a task handler H; P denotes a number of models; and i is a positive integer within [1,P].

It should be noted that for a text, audio, or image input task family, hPp may further include a necessary resource (such as audio or image) from previous context C. In this case, the context C is input into the dialogue engine L before parameter extraction.

The task family is determined by considering an input/output (I/O) mode by the task controller H.

$OP_p = P_p(\{q_n^{(s_1)}, q_n^{(s_2)}, \ldots, q_n^{(s_k)}\}, hP_p)$.

Optionally, in this embodiment, the basic models for the downstream task include a visual task model and an audio task model. The visual task model is configured to detect and segment a biomarker in a medical image, and is further configured to analyze and acquire blood pressure, heart rate, and health indicator parameters based on a facial video. For example, the basic models for the downstream task include a health prediction basic model, which receives a video and outputs a predicted physiological indicator such as predicted blood pressure and heart rate. They are implemented through a deep network. The audio task model is configured to identify audio.

S203. In a third stage, downstream task result feedback is performed. That is, the MFM executes the model Pp to generate a task output result oPp, and feeds back the task output result oPp to the MMF.

The MFM includes a series of basic models for processing a downstream task, and the MLM. It should be noted that a dialogue query may involve one or more task types. Multiple basic models of the MFM can be invoked for processing the downstream task in parallel according to actual needs, which improves processing efficiency.

The MLM can include a GPT model's gpt-3.5-turbo large-scale language model and a traditional knowledge chat robot, which are pre-trained based on an existing entity annotated medical question answering dialogue dataset.

S204. In a fourth stage, modal transformation normalization is performed. That is, the MLM extracts an entity-related text span from the task output result oPp sent by the MMF to acquire a structured entity, annotates the structured entity to generate a feedback text, and feeds back the feedback text to the MMF.

Specifically, first, the entity-related text span from the multimodal output result received by the MMF is extracted. Specifically, a built-in structured retriever can be used to perform entity retrieval on the knowledge base, acquire some entity-related attributes from the knowledge base, and annotate a corresponding standardized entity. Specifically, an annotation includes but is not limited to a disease, a symptom, a medicine, an examination, and an attribute.

S205. In a fifth stage, response generation is performed. The MLM receives a query result transmitted by the MMF, generates a professional response corresponding to the query result based on a medical knowledge base, and feeds back the professional response to a user.

It should be noted that response generation is highly correlated with the selected task Pp and the task output result oPp.

In a specific optional implementation, the professional response corresponding to the query result is generated based on the medical knowledge base, and the professional response is fed back to the user as follows.

In terms of an audio task, a waveform of a displayed image and an identification result of corresponding audio is output, and corresponding text information is generated as the professional response corresponding to the query result for feedback.

In terms of a text task, a transcribed text is fed back as the professional response corresponding to the query result for feedback.

In terms of a visual task, an output video and a related image frame is displayed, a corresponding visual task model of the MFM is invoked, a result is fed back to the MMF, and the MMF generates a text dialogue based on modal transformation of the result, as the professional response corresponding to query result for feedback.

In terms of a medical image tumor detection task, a segmented posterior image within a time span is displayed, and the MLM generates a corresponding text content based on an image segmentation result, as the professional response corresponding to the query result for feedback.

Specifically, in this embodiment, the multimodal task is not limited to image and text, but takes into account the task analysis and processing of image, text, audio, and video. The output result is fed back to the user in the form of multiple rounds of dialogue, achieving strong interpretability.

In this embodiment, the medical large model includes a multimodal transformer T, a prompt manager M, a dialogue engine L, a task controller H, and an MMF. The MMF includes at least one MFM. The present disclosure designs five stages, namely modal analysis, model allocation, downstream task result feedback, modal transformation normalization, and response generation. The present disclosure processes multimodal data simultaneously and fully utilizes the correlation between the multimodal data to achieve rapid multimodal task processing, improving the intelligent processing level and processing efficiency for artificial intelligence (AI) tasks.

It should be understood that the serial number of each step in the above embodiment does not indicate the order of performing the process. The order of performing each process is determined by its function and internal logic, and should not limit the implementation of the embodiments of the present disclosure.

Figure 4:
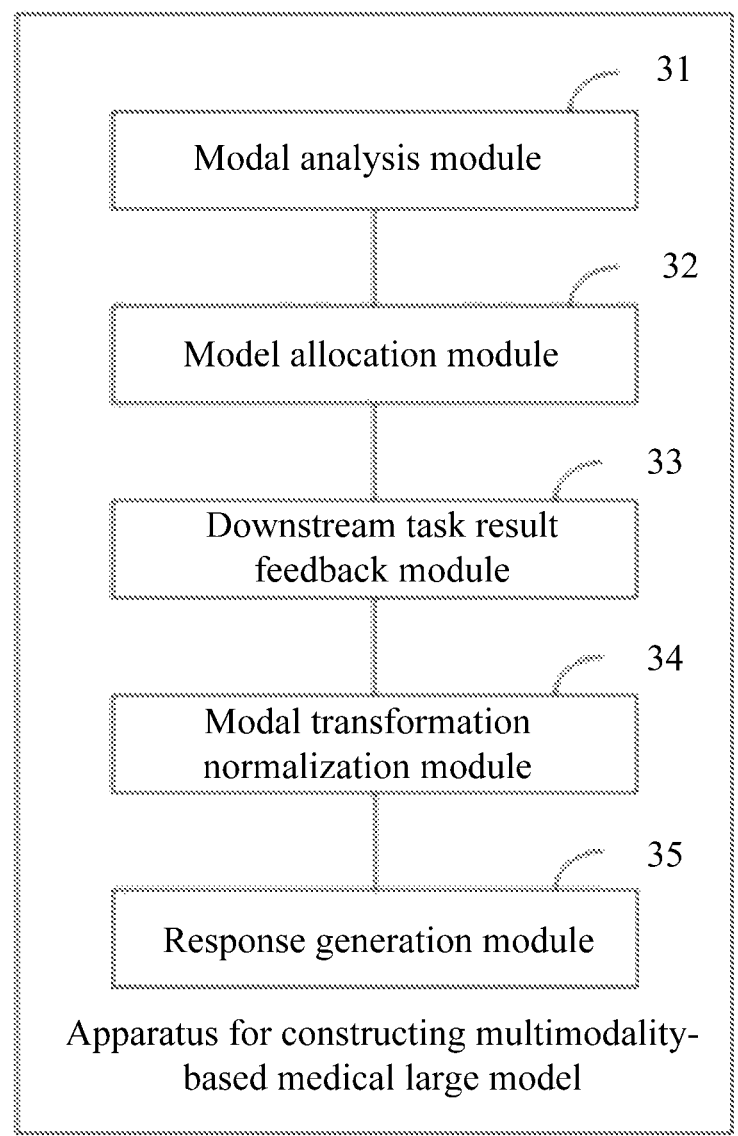
FIG. 4 is a structural diagram of an embodiment of an apparatus for constructing a multimodality-based medical large model according to the present disclosure.

FIG. 4 is a schematic diagram of an apparatus for constructing a multimodality-based medical large model, which corresponds to the method for constructing a multimodality-based medical large model according to the above embodiment. As shown in FIG. 4, the apparatus for constructing a multimodality-based medical large model includes modal analysis module 31, model allocation module 32, downstream task result feedback module 33, modal transformation normalization module 34, and response generation module 35. Each of the functional modules is described in detail below.

The modal analysis module 31 is configured to perform, by the multimodal transformer T, modal analysis on input query information to determine a task type.

The model allocation module 32 is configured to select, by the task controller H and the prompt manager M, a model Pp and a corresponding parameter hPp for task processing, and allocate a resource corresponding to the task type to the model Pp, where the model Pp is one of the basic models for the downstream task.

The downstream task result feedback module 33 is configured to, execute, by the MFM, the model Pp to generate a task output result oPp, and feed back the task output result oPp to the MMF.

The modal transformation normalization module 34 is configured to extract, by the MLM, an entity-related text span from the task output result oPp sent by the MMF to acquire a structured entity; annotate the structured entity to generate a feedback text; and feed back the feedback text to the MMF.

The response generation module 35 is configured to receive, by the MLM, a query result transmitted by the MMF, generate a professional response corresponding to the query result based on a medical knowledge base, and feed back the professional response to a user.

Optionally, the modal analysis module 31 includes an information transformation sub-module and a modal check sub-module.

The information transformation sub-module is configured to transform, by the multimodal transformer T, the input query information into query description $q_n^{(d)}$ and a set of query-related resources $\{q_n^{(s1)}, q_n^{(s2)}, \ldots, q_n^{(sk)}\}$ of size k, where the query description $q_n^{(d)}$ is in vectorized form, and input query information is in form of at least one of text, audio, and image.

The modal check sub-module is configured to perform a modal check on the query description $q_n^{(d)}$ to determine the task type.

Optionally, the multimodal transformer T is provided with a discriminator, and the modal check sub-module includes: a semantical aligning unit and a discrimination unit.

The semantical aligning unit is configured to semantically align the query description $q_n^{(d)}$ to acquire a new query.

The discrimination unit is configured to discriminate, by the discriminator, the new query to determine the task type.

Optionally, the model allocation module 32 includes a task family determination unit and a model selection unit.

The task family determination unit is configured to determine, by task controller H, a type of each of query-related resources $\{q_n^{(s_1)}, q_n^{(s_2)}, \ldots, q_n^{(s_k)}\}$ to determine different task families.

The model selection unit is configured to transfer, for a selected task family, the query description $q_n^{(d)}$ corresponding to the task family to the prompt manager M to generate a parameter, including the selected model Pp and corresponding parameter hPp, where p denotes a task model set $\{p_i\}_{i=1}^P$ to which the selected model belongs; hPp denotes the task family selected by a task handler H; P denotes a number of models; and i is a positive integer within [1,P].

Preferably, the response generation module 35 includes a first generation unit, a second generation unit, a third generation unit, and a fourth generation unit.

The first generation unit is configured to output, in terms of an audio task, a waveform of a displayed image and an identification result of corresponding audio, and generate corresponding text information as the professional response corresponding to the query result for feedback.

The second generation unit is configured to feed back, in terms of a text task, a transcribed text as professional response corresponding to the query result for feedback.

The third generation unit is configured to display, in terms of a visual task, an output video and a related image frame, invoke a corresponding visual task model of the MFM, and feed back a result to the MMF; and generate, by the MMF, a text dialogue based on modal transformation of the result, as the professional response corresponding to the query result for feedback.

The fourth generation unit is configured to display, in terms of a medical image tumor detection task, a segmented posterior image within a time span, and generate, by the MLM, a corresponding text content based on an image segmentation result, as the professional response corresponding to the query result for feedback.

For specific limitations of the apparatus for constructing a multimodality-based medical large model, reference may be made to the above limitations of the method for constructing a multimodality-based medical large model, which will not be repeated herein. The modules of the apparatus for constructing a multimodality-based medical large model may be implemented in whole or in part by software, hardware, or any combination thereof. The modules may be embedded in or independent of a processor of a computer device in a form of hardware, or stored in a memory of the computer device in a form of software, such that the processor can easily invoke and execute corresponding operations of the modules.

Figure 5:
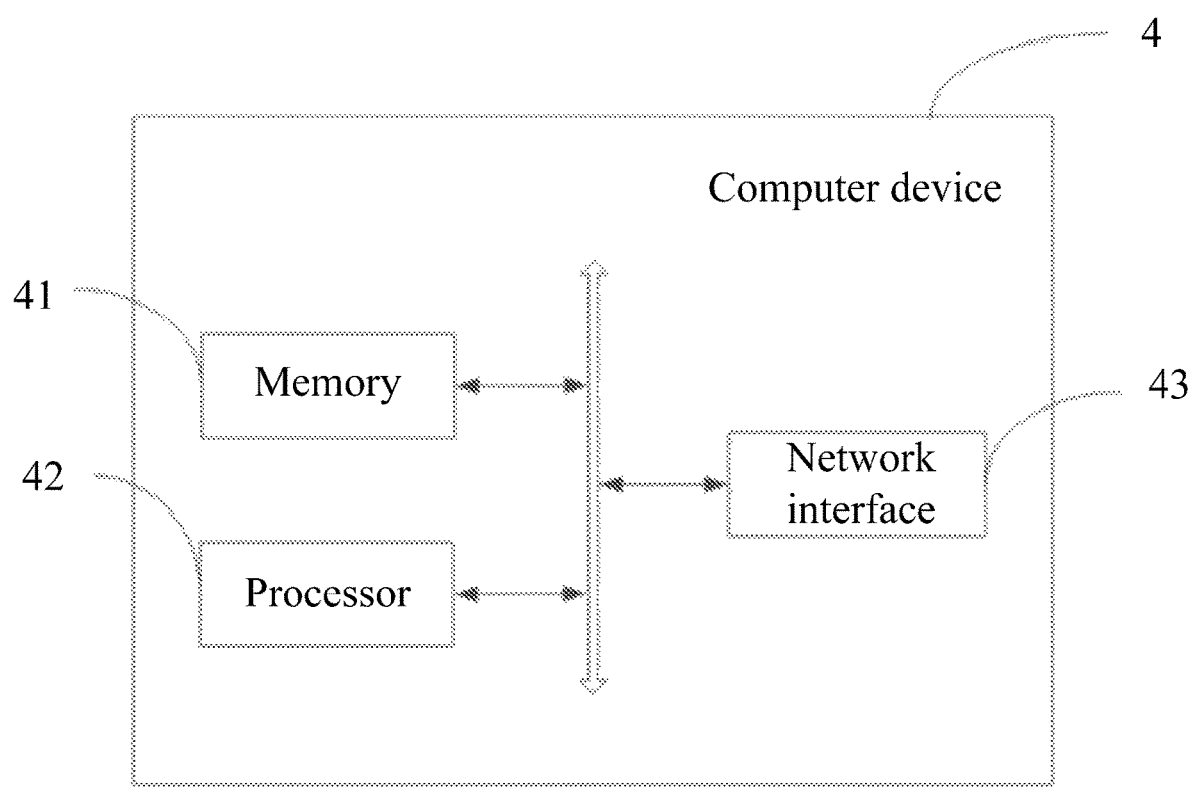
FIG. 5 is a structural diagram of an embodiment of a computer device according to the present disclosure.

In order to solve the above technical problem, an embodiment of the present disclosure further provides a computer device. Referring to FIG. 5, FIG. 5 is a basic structural block diagram of the computer device according to the embodiment.

The computer device 4 includes memory 41, processor 42, and network interface 43 that communicate through a system bus. It should be pointed out that the figure only shows the computer device 4 with the interconnected components such as the memory 41, the processor 42, and the network interface 43. However, it should be understood that it is not required to implement all the components shown, and more or fewer components can be alternatively implemented. Those skilled in this field should understand that the computer device here is a device that can automatically perform numerical calculations and/or information processing according to pre-set or stored instructions, and its hardware includes but is not limited to a microprocessor, an application specific integrated circuit (ASIC), a field-programmable gate array (FPGA), a digital processor (DSP), an embedded device, etc.

The computer device may be a computing device such as a desktop computer, a notebook, a palmtop computer or a cloud server. The computer device can interact with the user through a device such as a keyboard, a mouse, a remote control unit, a touchpad, or a voice controlled device.

The memory 41 includes at least one type of readable storage medium. The readable storage medium includes a flash memory, a hard disk, a multimedia card, a card type memory (such as a memory with secure digital (SD) or digital (D) interface display), a random access memory (RAM), a static random access memory (SRAM), a read-only memory (ROM), an electrically erasable programmable read-only memory (EEPROM), a programmable read-only memory (PROM), a magnetic memory, a magnetic disk, an optical disc, etc. In some embodiments, the memory 41 may be an internal storage unit of the computer device 4, such as a hard disk or memory of the computer device 4. In some other embodiments, the memory 41 may also be an external storage device of the computer device 4, such as a plug-in hard disk, a smart media card (SMC), a SD card, or a flash card that is provided on the computer device 4. Of course, the memory 41 may include both the internal storage unit and the external storage device of the computer device 4. In this embodiment, the memory 41 is typically configured to store an operating system and various application software installed on the computer device 4, such as program code for controlling an electronic file. In addition, the memory 41 may further be configured to temporarily store various data that has been output or will be output.

In some embodiments, the processor 42 may be a central processing unit (CPU), a controller, a microcontroller, a microprocessor, or other data processing chip. The processor 42 is typically configured to control the overall operation of the computer device 4. In this embodiment, the processor 42 is configured to run the program code stored in the memory 41 or process data, such as running program code built on the multimodality-based medical large model.

The network interface 43 may include a wireless network interface or a wired network interface, and the network interface 43 is typically configured to establish a communication connection between the computer device 4 and other electronic device.

The present disclosure further provides another implementation, that is, a computer-readable storage medium. The computer-readable storage medium stores a computer program, where the computer program is executed by at least one processor to implement the steps of the method for constructing a multimodality-based medical large model.

Through the foregoing description of the implementations, those skilled in the art can clearly understand that the foregoing method in the embodiments may be implemented by means of software and a necessary general-purpose hardware platform. Certainly, the hardware may be used, but the former is a better implementation manner in many cases. Based on this understanding, the technical solution of the present disclosure essentially, or a part contributing to the prior art, may be embodied in a form of a software product. The computer software product is stored on a storage medium (such as a ROM/RAM, a magnetic disk, an optical disk), and includes several instructions to enable a terminal device (may be a mobile phone, a computer, a server, or a network device) to execute the method according to each embodiment of the present disclosure.

Apparently, the embodiments described above are merely a part rather than all of the embodiments of the present disclosure. Preferred embodiments of the present disclosure are provided in the drawings, and are not intended to limit the scope of the present disclosure. The present disclosure may be implemented in many different forms. The embodiments are provided such that the disclosure of the present disclosure will be understood more thoroughly and comprehensively. Although the present disclosure is described in detail with reference to the foregoing embodiments, those skilled in the art can still make modifications to the technical solutions described in the foregoing embodiments, or make equivalent replacement to some of the technical features. Any equivalent structure made by using the specification and the drawings of the present disclosure, or direct or indirect application thereof in other related technical fields, should still fall in the protection scope of the patent of the present disclosure.

What is claimed is:

1. A method for constructing a multimodality-based medical large model, wherein the multimodality-based medical large model comprises a multimodal transformer T, a prompt manager M, a dialogue engine L, a task controller H, and a multimodal foundation (MMF); the MMF comprises at least one medical foundation model (MFM); the MFM comprises basic models for a downstream task, and a medical language module (MLM); and the method for constructing the multimodality-based medical large model comprises:
   in a first stage, modal analysis: performing, by the multimodal transformer T, modal analysis on input query information to determine a task type;
   in a second stage, model allocation: selecting, by the task controller H and the prompt manager M, a model Pp and a corresponding parameter hPp for task processing, and allocating a resource corresponding to the task type to the model Pp, wherein the model Pp is one of the basic models for the downstream task, P denotes a number of models, p denotes a task model set to which the selected model belongs, and the parameter hPp denotes a task family selected by a task handler H;
   in a third stage, downstream task result feedback: executing, by the MFM, the model Pp to generate a task output result oPp, and feeding back the task output result oPp to the MMF;
   in a fourth stage, modal transformation normalization: extracting, by the MLM, an entity-related text span from the task output result oPp sent by the MMF to acquire a structured entity; annotating the structured entity to generate a feedback text; and feeding back the feedback text to the MMF; and
   in a fifth stage, response generation: receiving, by the MLM, a query result transmitted by the MMF, generating a professional response corresponding to the query result based on a medical knowledge base, and feeding back the professional response to a user;
   wherein the step of performing, by the multimodal transformer T, the modal analysis on the input query information to determine the task type comprises:
   transforming, by the multimodal transformer T, the input query information into a query description $q_n^{(d)}$ and a set of query-related resources $\{q_n^{(s_1)}, q_n^{(s_2)}, \ldots, q_n^{(s_k)}\}$ of size k, wherein the query description $q_n^{(d)}$ is in vectorized form, and the input query information is in form of at least one of text, audio, and image; and $s_1$ to $s_k$ denote serial numbers of the query-related sources; and
   performing a modal check on the query description $q_n^{(d)}$ to determine the task type.

2. The method for constructing the multimodality-based medical large model according to claim 1, wherein the multimodal transformer T is provided with a discriminator, and the step of performing a modal check on the query description $q_n^{(d)}$ to determine the task type comprises:
   semantically aligning the query description $q_n^{(d)}$ to acquire a new query; and
   discriminating, by the discriminator, the new query to determine the task type.

3. The method for constructing the multimodality-based medical large model according to claim 1, wherein the step of selecting, by the task controller H and the prompt manager M, the model Pp and the corresponding parameter hPp for the task processing comprises:
   determining, by the task controller H, a type of each of the query-related resources $\{q_n^{(s_1)}, q_n^{(s_2)}, \ldots, q_n^{(s_k)}\}$ to determine different task families; and
   transferring, for a selected task family, the query description $q_n^{(d)}$ corresponding to the task family to the prompt manager M to generate a parameter, comprising the selected model Pp and corresponding parameter hPp, wherein p denotes a task model set $\{p_i\}_{i=1}^{P}$ to which the selected model belongs; hPp denotes the task family selected by the task handler H; P denotes a number of models; and i is a positive integer within [1,P].

4. The method for constructing the multimodality-based medical large model according to claim 3, wherein the basic models for the downstream task comprise a visual task model and an audio task model; the visual task model is configured to detect and segment a biomarker in a medical image, and is further configured to analyze and acquire blood pressure, heart rate, and health indicator parameters based on a facial video; and the audio task model is configured to identify audio.

5. The method for constructing the multimodality-based medical large model according to claim 1, wherein the step of generating the professional response corresponding to the query result based on the medical knowledge base, and feeding back the professional response to the user comprises:
   outputting, in terms of an audio task, a waveform of a displayed image and an identification result of corresponding audio, and generating corresponding text information as the professional response corresponding to the query result for feedback;
   feeding back, in terms of a text task, a transcribed text as the professional response corresponding to the query result for feedback;
   displaying, in terms of a visual task, an output video and a related image frame; invoking a corresponding visual task model of the MFM, and feeding back a result to the MMF; and generating, by the MMF, a text dialogue based on modal transformation of the result, as the professional response corresponding to the query result for feedback; and
   displaying, in terms of a medical image tumor detection task, a segmented posterior image within a time span, and generating, by the MLM, a corresponding text content based on an image segmentation result, as the professional response corresponding to the query result for feedback.

6. The method for constructing the multimodality-based medical large model according to claim 2, wherein the step of selecting, by the task controller H and the prompt manager M, the model Pp and the corresponding parameter hPp for the task processing comprises:
  determining, by the task controller H, a type of each of the query-related resources $\{q_n^{(s1)}, q_n^{(s2)}, \ldots, q_n^{(sk)}\}$ to determine different task families; and
  transferring, for a selected task family, the query description $q_n^{(d)}$ corresponding to the task family to the prompt manager M to generate a parameter, comprising the selected model Pp and corresponding parameter hPp, wherein p denotes a task model set $\{p_i\}_{i=1}^{P}$ to which the selected model belongs; hPp denotes the task family selected by the task handler H; P denotes a number of models; and i is a positive integer within [1,P].

7. The method for constructing the multimodality-based medical large model according to claim 2, wherein the step of generating the professional response corresponding to the query result based on the medical knowledge base, and feeding back the professional response to the user comprises:
  outputting, in terms of an audio task, a waveform of a displayed image and an identification result of corresponding audio, and generating corresponding text information as the professional response corresponding to the query result for feedback;
  feeding back, in terms of a text task, a transcribed text as the professional response corresponding to the query result for feedback;
  displaying, in terms of a visual task, an output video and a related image frame; invoking a corresponding visual task model of the MFM, and feeding back a result to the MMF; and generating, by the MMF, a text dialogue based on modal transformation of the result, as the professional response corresponding to the query result for feedback; and
  displaying, in terms of a medical image tumor detection task, a segmented posterior image within a time span, and generating, by the MLM, a corresponding text content based on an image segmentation result, as the professional response corresponding to the query result for feedback.

8. The method for constructing the multimodality-based medical large model according to claim 3, wherein the step of generating the professional response corresponding to the query result based on the medical knowledge base, and feeding back the professional response to the user comprises:
  outputting, in terms of an audio task, a waveform of a displayed image and an identification result of corresponding audio, and generating corresponding text information as the professional response corresponding to the query result for feedback;
  feeding back, in terms of a text task, a transcribed text as the professional response corresponding to the query result for feedback;
  displaying, in terms of a visual task, an output video and a related image frame; invoking a corresponding visual task model of the MFM, and feeding back a result to the MMF; and generating, by the MMF, a text dialogue based on modal transformation of the result, as the professional response corresponding to the query result for feedback; and
  displaying, in terms of a medical image tumor detection task, a segmented posterior image within a time span, and generating, by the MLM, a corresponding text content based on an image segmentation result, as the professional response corresponding to the query result for feedback.

9. The method for constructing the multimodality-based medical large model according to claim 4, wherein the step of generating the professional response corresponding to the query result based on the medical knowledge base, and feeding back the professional response to the user comprises:
  outputting, in terms of an audio task, a waveform of a displayed image and an identification result of corresponding audio, and generating corresponding text information as the professional response corresponding to the query result for feedback;
  feeding back, in terms of a text task, a transcribed text as the professional response corresponding to the query result for feedback;
  displaying, in terms of a visual task, an output video and a related image frame; invoking a corresponding visual task model of the MFM, and feeding back a result to the MMF; and generating, by the MMF, a text dialogue based on modal transformation of the result, as the professional response corresponding to the query result for feedback; and
  displaying, in terms of a medical image tumor detection task, a segmented posterior image within a time span, and generating, by the MLM, a corresponding text content based on an image segmentation result, as the professional response corresponding to the query result for feedback.

10. A computer device, comprising a memory, a processor, and a computer program stored in the memory and executable on the processor, wherein the processor executes the computer program to implement the method for constructing the multimodality-based medical large model according to claim 1.

11. The computer device according to claim 10, wherein in the method, the multimodal transformer T is provided with a discriminator, and the step of performing a modal check on the query description $q_n^{(d)}$ to determine the task type comprises:
  semantically aligning the query description $q_n^{(d)}$ to acquire a new query; and
  discriminating, by the discriminator, the new query to determine the task type.

12. The computer device according to claim 10, wherein in the method, the step of selecting, by the task controller H and the prompt manager M, the model Pp and the corresponding parameter hPp for the task processing comprises:
  determining, by the task controller H, a type of each of the query-related resources $\{q_n^{(s1)}, q_n^{(s2)}, \ldots, q_n^{(sk)}\}$ to determine different task families; and
  transferring, for a selected task family, the query description $q_n^{(d)}$ corresponding to the task family to the prompt manager M to generate a parameter, comprising the selected model Pp and corresponding parameter hPp, wherein p denotes a task model set $\{p_i\}_{i=1}^{P}$ to which the selected model belongs; hPp denotes the task family selected by the task handler H; P denotes a number of models; and i is a positive integer within [1,P].

13. The computer device according to claim 12, wherein in the method, the basic models for the downstream task comprise a visual task model and an audio task model, wherein the visual task model and the audio task model are software models; the visual task model is configured to detect and segment a biomarker in a medical image, and is further configured to analyze and acquire blood pressure, heart rate, and health indicator parameters based on a facial video; and the audio task model is configured to identify audio.

14. The computer device according to claim 10, wherein in the method, the step of generating the professional response corresponding to the query result based on the medical knowledge base, and feeding back the professional response to the user comprises:
- outputting, in terms of an audio task, a waveform of a displayed image and an identification result of corresponding audio, and generating corresponding text information as the professional response corresponding to the query result for feedback;
- feeding back, in terms of a text task, a transcribed text as the professional response corresponding to the query result for feedback;
- displaying, in terms of a visual task, an output video and a related image frame; invoking a corresponding visual task model of the MFM, and feeding back a result to the MMF; and generating, by the MMF, a text dialogue based on modal transformation of the result, as the professional response corresponding to the query result for feedback; and
- displaying, in terms of a medical image tumor detection task, a segmented posterior image within a time span, and generating, by the MLM, a corresponding text content based on an image segmentation result, as the professional response corresponding to the query result for feedback.

15. A non-transitory computer-readable storage medium, storing a computer program, wherein the computer program is executed by a processor to implement the method for constructing the multimodality-based medical large model according to claim 1.

16. The non-transitory computer-readable storage medium according to claim 15, wherein in the method, the multimodal transformer T is provided with a discriminator, and the step of performing a modal check on the query description $q_n^{(d)}$ to determine the task type comprises:
- semantically aligning the query description $q_n^{(d)}$ to acquire a new query; and
- discriminating, by the discriminator, the new query to determine the task type.

17. The non-transitory computer-readable storage medium according to claim 15, wherein in the method, the step of selecting, by the task controller H and the prompt manager M, the model Pp and the corresponding parameter hPp for the task processing comprises:
- determining, by the task controller H, a type of each of the query-related resources $\{q_n^{(s1)}, q_n^{(s2)}, \ldots, q_n^{(sk)}\}$ to determine different task families; and
- transferring, for a selected task family, the query description $q_i$ corresponding to the task family to the prompt manager M to generate a parameter, comprising the selected model Pp and corresponding parameter hPp, wherein p denotes a task model set $\{p_i\}_{i=1}^{P}$ to which the selected model belongs; hPp denotes the task family selected by the task handler H; P denotes a number of models; and i is a positive integer within [1,P].

18. The non-transitory computer-readable storage medium according to claim 17, wherein in the method, the basic models for the downstream task comprise a visual task model and an audio task model, wherein the visual task model and the audio task model are software models; the visual task model is configured to detect and segment a biomarker in a medical image, and is further configured to analyze and acquire blood pressure, heart rate, and health indicator parameters based on a facial video; and the audio task model is configured to identify audio.

19. An apparatus for constructing a multimodality-based medical large model, the apparatus comprises a processor and a memory, wherein the multimodality-based medical large model comprises a multimodal transformer T, a prompt manager M, a dialogue engine L, a task controller H, and a multimodal foundation (MMF); the MMF comprises at least one medical foundation model (MFM); the MFM comprises basic models for a downstream task, and a medical language module (MLM); and the memory comprises the following software modules:
- a modal analysis module, configured to perform, by the multimodal transformer T, modal analysis on input query information to determine a task type;
- a model allocation module, configured to select, by the task controller H and the prompt manager M, a model Pp and a corresponding parameter hPp for task processing, and allocate a resource corresponding to the task type to the model Pp, wherein the model Pp is one of the basic models for the downstream task, P denotes a number of models, p denotes a task model set to which the selected model belongs, and the parameter hPp denotes a task family selected by a task handler H;
- a downstream task result feedback module, configured to, execute, by the MFM, the model Pp to generate a task output result oPp, and feed back the task output result oPp to the MMF;
- a modal transformation normalization module, configured to extract, by the MLM, an entity-related text span from the task output result oPp sent by the MMF to acquire a structured entity; annotate the structured entity to generate a feedback text; and feed back the feedback text to the MMF; and
- a response generation module, configured to receive, by the MLM, a query result transmitted by the MMF, generate a professional response corresponding to the query result based on a medical knowledge base, and feed back the professional response to a user; wherein the modal analysis module comprises:
- an information transformation sub-module, configured to transform, by the multimodal transformer T, the input query information into a query description $q_n^{(d)}$ and a set of query-related resources $\{q_n^{(s1)}, q_n^{(s2)}, \ldots, q_n^{(sk)}\}$ of size k, wherein the query description $q_n^{(d)}$ is in vectorized form, and the input query information is in form of at least one of text, audio, and image; and
- a modal check sub-module, configured to perform a modal check on the query description $q_n^{(d)}$ to determine the task type;
- wherein the modal analysis module, the model allocation module, the downstream task result feedback module, the modal transformation normalization module, the response generation module, the information transformation sub-module, and the modal check sub-module are executed by the processor of the apparatus for performing the above functions.

20. The apparatus for constructing the multimodality-based medical large model according to claim 19, wherein the model allocation module comprises:
- a task family determination unit, configured to determine, by the task controller H, a type of each of the query-related resources $\{q_n^{(s1)}, q_n^{(s2)}, \ldots, q_n^{(sk)}\}$ to determine different task families; and
- a model selection unit, configured to transfer, for a selected task family, the query description $q_n^{(d)}$ corresponding to the task family to the prompt manager M to generate a parameter, comprising the selected model Pp and corresponding parameter hPp, wherein p denotes a task model set $\{p_i\}_{i=1}^{P}$ to which the selected model belongs; P denotes a number of models; i is a positive integer within [1,P]; and hPp denotes the task family selected by the task handler H.

* * * * *